(12) United States Patent
Rao et al.

(10) Patent No.: US 8,338,617 B2
(45) Date of Patent: Dec. 25, 2012

(54) PROCESS FOR PREPARING OXAZOLIDINE DERIVATIVES

(75) Inventors: Siripragada Mahender Rao, Hyderabad (IN); Ramanatham Josyula, Hyderabad (IN); C. Naveen Kumar Reddy, Hyderabad (IN); Veerababu Kagita, Hyderabad (IN); Yusuf Vohra, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 1084 days.

(21) Appl. No.: 11/577,945

(22) PCT Filed: Nov. 18, 2005

(86) PCT No.: PCT/US2005/041955
§ 371 (c)(1),
(2), (4) Date: Apr. 25, 2007

(87) PCT Pub. No.: WO2006/055837
PCT Pub. Date: May 26, 2006

(65) Prior Publication Data
US 2009/0131679 A1    May 21, 2009

(30) Foreign Application Priority Data
Nov. 19, 2004    (IN) .......................... 1223/CHE/2004

(51) Int. Cl.
*C07D 263/04*    (2006.01)

(52) U.S. Cl. ....................................................... 548/215

(58) Field of Classification Search .................... 548/215
See application file for complete search history.

(56) References Cited

U.S. PATENT DOCUMENTS

| | | |
|---|---|---|
| 5,292,921 A | 3/1994 | Correa et al. |
| 5,476,954 A | 12/1995 | Bourzat |
| 6,433,180 B1 | 8/2002 | Denis |

*Primary Examiner* — Kamal A Saeed
*Assistant Examiner* — Kristin Bianchi
(74) *Attorney, Agent, or Firm* — Robert A. Franks; Lee C. Banks; Anjum Swaroop

(57) ABSTRACT

A process for preparing (4S,5R)-5-carboxymethyl-2,2-dimethyl-4-phenyl-oxazolidine-3-carboxylic acid t-butyl ester, an intermediate in the preparation of anticancer compounds having a taxane skeleton, such as paclitaxel, docetaxol, etc.

20 Claims, No Drawings

PROCESS FOR PREPARING OXAZOLIDINE DERIVATIVES

INTRODUCTION TO THE INVENTION

The present invention relates to a process for the preparation of the oxazolidine derivative of Formula I.

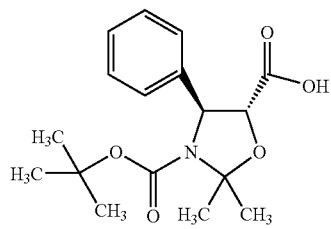

I

The compound of Formula I, having the chemical name (4S, 5R)-5-carboxymethyl-2,2-dimethyl-4-phenyl-oxazolidine-3-carboxylic acid t-butyl ester, is useful as an intermediate for preparing anticancer compounds having a taxane skeleton, such as paclitaxel, docetaxol, etc.

The taxane families of terpenes are considered to be potent anti-tumor chemotherapeutics having a broad spectrum of anti-leukemia and anti-tumor activity. Accordingly, there has been much interest in this compound in both the areas of biology and chemistry. Oxazolidine derivatives can be coupled with taxane derivatives to prepare paclitaxel.

U.S. Pat. No. 5,476,954 discloses an oxazolidine derivative of Formula I prepared by a process that requires reacting a dimethoxyalkane with a phenylisoserine ester derivative. The process involves a large number of reaction steps for the preparation of the compound. Chemical substances like sodium adize and di-n-butylboron triflate used in this process are difficult to handle on a plant scale. The process disclosed in this patent is described in reaction Scheme 1.

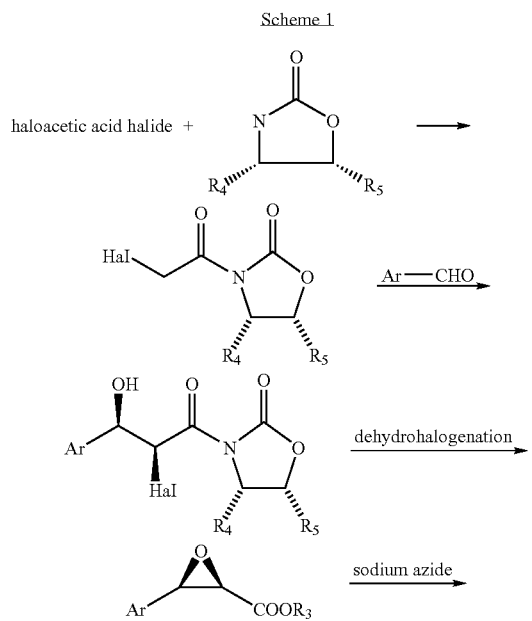

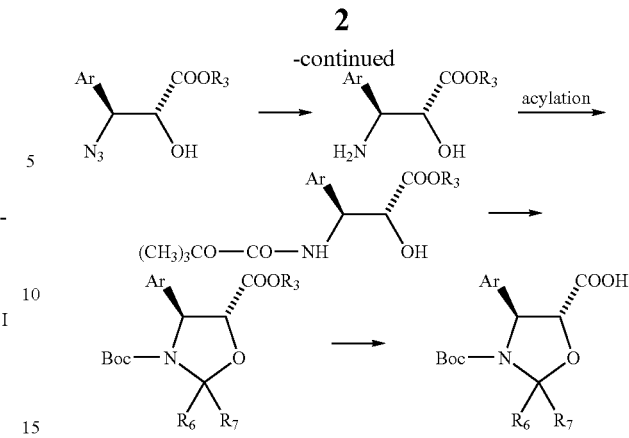

U.S. Pat. No. 5,292,921 discloses a process for an enantioselective preparation of the phenylisoserine derivative of Formula (d), wherein the starting material is phenylglycine and involves a Swern oxidation, carried out under cryogenic conditions in the presence of an oxalyl chloride/dimethyl sulfoxide mixture, which is quite cumbersome and results in at least 5% of racemization. The process is described in reaction Scheme 2.

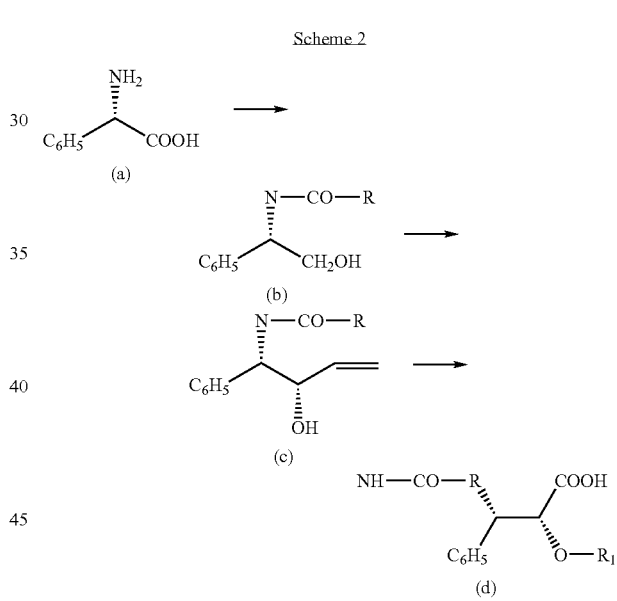

The process uses a starting material that results in an increased number of reaction steps. U.S. Pat. No. 6,433,180, granted to the same group of inventors, discloses the process of preparation of an isomer (i.e., 4S,5S) of the compound of Formula I which is prepared by using the compound of Formula (d) of the U.S. Pat. No. 5,292,921 patent. The above processes give comparatively low yield, and are difficult to operate for commercial scale production.

There remains a need for a process that is highly stereoselective, easy to operate on a production scale, and gives a high product yield.

SUMMARY OF THE INVENTION

An aspect of the invention includes a process comprising:
(i) reacting phenylglycinol with a reagent for introducing a t-butoxycarbonyl group, to produce (1S)-(2-hydroxy-1-phenyl-ethyl)-carbamic acid t-butyl ester;

(ii) oxidizing the product of (i) and then reacting an obtained carbonyl intermediate with vinyl magnesium halide to produce (1S,2S)-(2-hydroxy-1-phenyl-but-3-enyl)carbamic acid t-butyl ester;

(iii) reacting the product of (ii) with 2,2-dimethoxypropane to produce (4S,5R)-2,2-dimethyl-4-phenyl-5-vinyl-oxazolidine-3-carboxylic acid t-butyl ester; and (iv) oxidizing the product of (iii) to form (4S,5R)-5-carboxymethyl-2,2-dimethyl-4-phenyl-oxazolidine-3-carboxylic acid t-butyl ester.

An additional aspect of the invention includes a process comprising:

(i) reacting phenylglycinol with di-t-butyl dicarbonate, to produce (1S)-(2-hydroxy-1-phenyl-ethyl)-carbamic acid t-butyl ester;

(ii) reacting the product of (i) with a hypochlorite compound, and then reacting an obtained carbonyl intermediate with vinyl magnesium halide to produce (1S,2S)-(2-hydroxy-1-phenyl-but-3-enyl)carbamic acid t-butyl ester;

(iii) reacting the product of (ii) with 2,2-dimethoxypropane to produce (4S,5R)-2,2-dimethyl-4-phenyl-5-vinyl-oxazolidine-3-carboxylic acid t-butyl ester;

(iv) purifying (4S,5R)-2,2-dimethyl-4-phenyl-5-vinyl-oxazolidine-3-carboxylic acid t-butyl ester; and (v) reacting purified (4S,5R)-2,2-dimethyl-4-phenyl-5-vinyl-oxazolidine-3-carboxylic acid t-butyl ester with an alkali metal periodate to produce (4S,5R)-5-carboxymethyl-2,2-dimethyl-4-phenyl-oxazolidine-3-carboxylic acid t-butyl ester.

In a further aspect, the invention includes a process for preparing the compound of Formula I

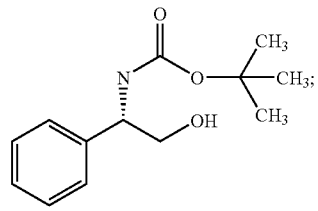

I comprising:

(i) reacting phenylglycinol with a reagent for introducing a t-butoxycarbonyl group, to obtain the compound of Formula II

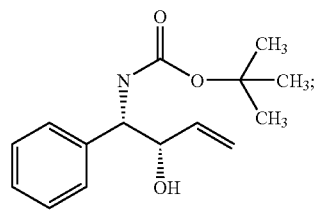

(II)

(ii) oxidizing the compound of Formula II and then reacting an obtained carbonyl intermediate with vinyl magnesium halide to obtain the compound of Formula III

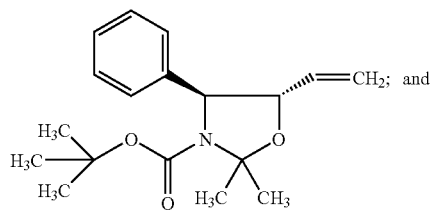

(III)

(iii) reacting the compound of Formula III with 2,2-dimethoxypropane to obtain the compound of Formula IV

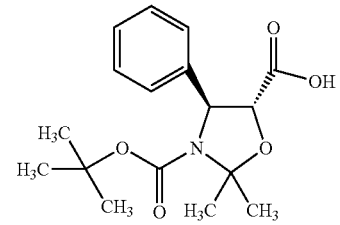

(IV)

(iv) oxidizing the compound of Formula IV.

In an embodiment of the process, the compound of Formula IV is purified prior to oxidizing in (iv).

DETAILED DESCRIPTION

The present invention relates to a process for the preparation of an oxazolidine derivative of Formula I,

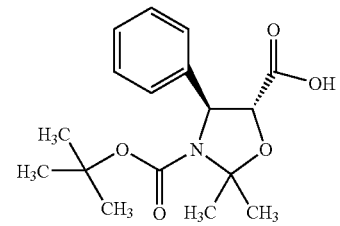

I which is useful for preparing anticancer compounds having a taxane skeleton, such as paclitaxel, docetaxol etc.

In accordance with the invention, a process for preparing the compound of Formula I

I comprises:

(i) protecting the amino group of phenylglycinol by reacting with a reagent for introducing a t-butoxycarbonyl group, to obtain the compound of Formula II;

(ii) oxidizing the compound of Formula II and then reacting the obtained carbonyl intermediate with vinyl magnesium halide to obtain the compound of Formula III;

(iii) reacting the compound of Formula III with 2,2-dimethoxypropane to obtain the compound of Formula IV; and (iv) oxidizing the compound of Formula IV.

A process for the preparation of the compound of Formula I is shown in reaction Scheme 3, wherein the structures of these compounds are included.

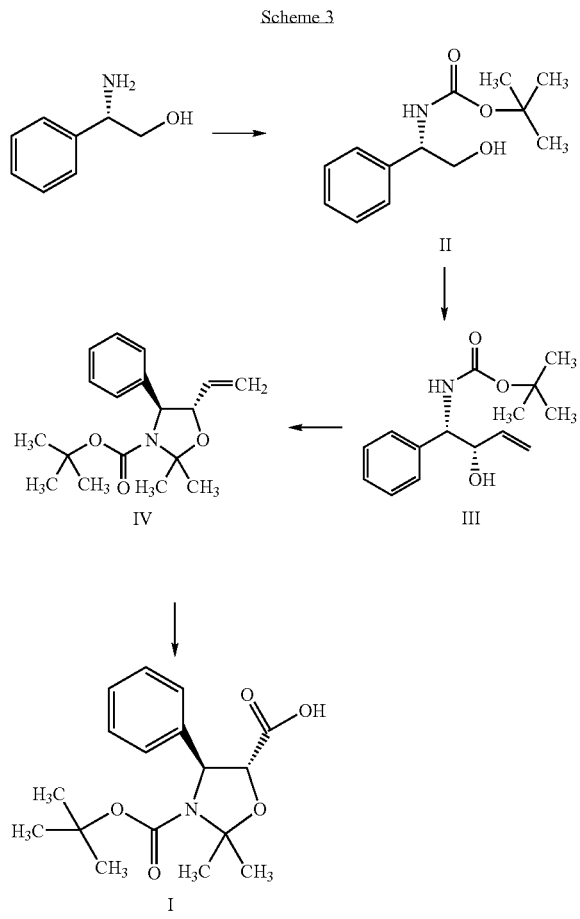

An embodiment of a process for preparing the compound having Formula I comprises the above steps, using the reagents and conditions that are described below.

Step (i)

Phenylglycinol is dissolved in a polar solvent and a base, such as sodium bicarbonate or potassium bicarbonate, is added at a temperature in the range of about 10° C. to 60° C. A solution providing a t-butoxycarbonyl group, such as Boc anhydride (di-t-butyl dicarbonate), in a polar solvent is slowly added over a period of about 20-50 minutes, followed by stirring at about 20-40° C. until the reaction is complete, such as for about 20-40 minutes. After completion of the reaction, water is added to the reaction mass. The organic layer is separated and concentrated under reduced pressure to the minimum volume that maintains a solution, petroleum ether is added and the mixture is stirred, such as for about 10-50 minutes, then the formed solid is filtered and dried at a temperature in the range of about 40° C.-70° C. to obtain (1S)-(2-hydroxy-1-phenyl-ethyl)-carbamic acid t-butyl ester.

In this step, useful polar solvents include, without limitation: esters such as ethyl acetate and methyl acetate; halogenated hydrocarbons such as dichloromethane and ethylene dichloride; and the like.

Useful bases include, without limitation, sodium bicarbonate, potassium bicarbonate, sodium hydroxide, potassium hydroxide, and the like.

Step (ii)

(1S)-(2-Hydroxy-1-phenyl-ethyl)carbamic acid t-butyl ester is dissolved in a polar solvent and water. To this, sodium bromide is added. The reaction mixture is cooled to about −7° C. to 0° C. and 2,2,6,6-tetramethylpiperidine-N-oxide ("TEMPO") oxidation catalyst is added. The reaction mixture is stirred for a short period, such as about 5 to 25 minutes, and, at the same temperature, a mixture of a hypochlorite solution (such as a sodium hypochlorite solution having a pH of about 8.5 to 9.5), sodium bicarbonate, and water is added dropwise over a period of about 30-90 minutes at about −7° C. to 5° C. and stirred for about 5-20 minutes. Water is added to the reaction mass and the organic layer is separated and dried to produce a "Reaction Mass 1."

Useful polar solvents include, without limitation: halogenated hydrocarbons such as dichloromethane and dichloroethane; esters such as ethylacetate; ethers such as tetrahydrofuran; dimethylsulfoxide; and the like.

Vinyl magnesium bromide solution is placed under an inert atmosphere, such as under nitrogen. Dichloromethane is slowly added, then the mixture is cooled to about 25° C. Reaction Mass 1 in dichloromethane is added dropwise over a period of about 30 minutes. After addition, the reaction mixture is stirred at a temperature in the range of about 20-40° C. until reaction completion, such as for a time period in the range of about 1-3 hours. The completion of reaction is confirmed by TLC. Aqueous ammonium chloride solution is added to the reaction mass at about 5-20° C. Dichloromethane is added to the reaction mass and the separated organic layer is washed with dilute hydrochloric acid solution, sodium bicarbonate solution, and brine solution. The organic layer is concentrated at 45° C. under vacuum to produce a thick semi-solid (1S,2S)-(2-hydroxy-1-phenyl-but-3-enyl)carbamic acid t-butyl ester.

Step (iii)

(1S,2S)-(2-hydroxy-1-phenyl-but-3-enyl)carbamic acid t-butyl ester is dissolved in an aromatic solvent. 2,2-Dimethoxypropane is added at a temperature in the range of about 20-40° C. followed by addition of pyridinium p-toluene sulfonate. The reaction mixture is heated to about 70-95° C. and stirred at the same temperature for about 1-5 hours. The reaction mixture is cooled to about 30 to 45° C., neutralized with pyridine, and concentrated under reduced pressure to get (4S,5R)-2,2-dimethyl-4-phenyl-5-vinyl-oxazolidine-3-carboxylic acid t-butyl ester in a semi solid form, which is optionally further purified by column chromatography, such as using petroleum ether and ethyl acetate as solvents.

Useful aromatic solvents include, without limitation, toluene, xylene, chlorobenzene, dichlorobenzene, chlorotoluene, benzonitrile, benzotrifluoride, and the like.

Step (iv)

(4S,5R)-2,2-Dimethyl-4-phenyl-5-vinyl-oxazolidine-3-carboxylic acid t-butyl ester is dissolved in a polar solvent. Carbon tetrachloride and water are added, followed by the addition of a base such as sodium hydroxide, potassium hydroxide, sodium carbonate, or sodium bicarbonate, at a temperature in the range of about 10-50° C. The reaction mixture is stirred for about 10 to 20 minutes and an alkali metal periodate, such as sodium metaperiodate, is added in small portions to the reaction mixture, such as over a period of about 20 to 40 minutes. A ruthenium salt catalyst, such as ruthenium trichloride, is added to the reaction mixture at a temperature in the range of about 20-40° C. and stirred to reaction completion, such as for about 30-40 hours. The reaction mass is filtered and the filtrate is washed with ethyl acetate, then the aqueous layer is cooled to about 10-15° C. and acidified with 10% aqueous hydrochloric acid to pH 2-3. The aqueous layer is extracted with ethyl acetate, then the organic layer is washed with a 2% aqueous $Na_2S_2O_3$ solution and washed with brine solution. The organic layer is concentrated at about 50° C. under vacuum to get a thick semi-solid. The solid is triturated with petroleum ether and filtered to get the desired white solid (4S,5R)-5-carboxymethyl-2,2-dimethyl-4-phenyl-oxazolidine-3-carboxylic acid t-butyl ester (I).

Useful polar solvents include, without limitation: acetonitrile; alcohols such as methanol and ethanol; halogenated hydrocarbons such as carbon tetrachloride and chloroform; ketones such as acetone and methyl iso-butyl ketone; and the like.

In the foregoing discussion, certain temperature and other reaction conditions, and reaction times, have been given. However, these are not the only conditions and times that can be used in the successful practice of the invention, and appropriate modifications will be readily apparent to those having skill in the art. For example, many reactions will proceed at a higher rate if the temperature is increased, resulting in a shorter reaction time period, and in many instances reaction conditions can be maintained beyond the times given in the discussion. Where reagents are added in small increments for reaction, the times suggested in this description can be made shorter or linger, as will be readily apparent to those skilled in the art. All such modifications are considered to be within the scope of the invention.

The following examples are provided to further illustrate certain aspects and embodiments of the invention and the manner in which it may be carried out. It will be understood, however, that the specific details given in the examples have been chosen for purposes of illustration and are not to be construed as limiting the scope of the invention.

In the examples, purities were determined by high performance liquid chromatography, and the purity percentages are in area-% units.

EXAMPLE 1

Preparation of (1S)-(2-hydroxy-1-phenyl-ethyl)-carbamic acid tert-butyl ester (II)

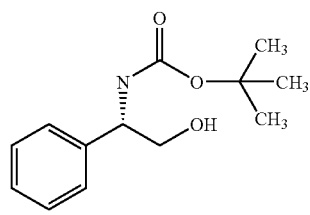

(II)

Phenylglycinol (250 grams, 1.82 mol) was dissolved in ethyl acetate (2.25 L). To the solution 306 g of sodium bicarbonate was added at a temperature in the range of 20° C. to 40° C. and the reaction mixture was stirred for 15 minutes. A solution of Boc anhydride (477 grams, 2.18 mole) in ethyl acetate (250 mL) was added slowly over a period of 30 minutes. After completion of the addition, the reaction mixture was stirred at a temperature in the range of 20-40° C. for 30 minutes. After completion of reaction, 4 L of water was added to the reaction mass. The organic layer was separated and concentrated to the minimum level for maintaining a solution, then petroleum ether (1.5 liters) was added and stirred for 30 minutes. The solid was separated by filtration and dried at 50° C. to get (1S)-(2-hydroxy-1-phenyl-ethyl)-carbamic acid tert-butyl ester.
Weight: 383 grams
Yield: 88%
Purity: 99.69%
Chiral purity: 99-100%

EXAMPLE 2

Preparation of (1S,2S)-(2-hydroxy-1-phenyl-but-3-enyl)-carbamic acid tert-butyl ester (III)

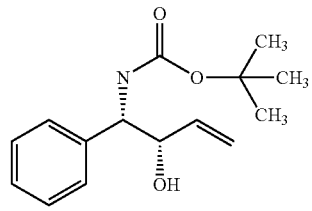

(III)

Step 1

(1S)-(2-Hydroxy-1-phenyl-ethyl)-carbamic acid t-butyl ester (150 grams, 0.632 mole) was dissolved in dichloromethane (DCM) (2.4 L), and water (600 mL), then sodium bromide (65.1 grams, 0.632 mole) was added. The reaction mixture was cooled to −5° C. and 2,2,6,6-tetramethylpiperidine-N-oxide (TEMPO) (0.99 grams, 0.006 mole) was added. The reaction mixture was stirred for 15 minutes and, at the same temperature, a mixture of 10-12% sodium hypochlorite solution (pH adjusted to 9) (840 mL), sodium bicarbonate (155 grams) and water (1200 mL) was added dropwise over 1 hour at −5° C. and then the mass was stirred for about 5-10 minutes. Water (5 L) was added to the reaction mass and the layers were separated. The organic layer was discarded and the aqueous layer was extracted with dichloromethane (1.5 L). The organic layer was washed with a solution of 5% aqueous $KHSO_4$ (500 mL) having 5 grams of KI, followed by water (1 L), 2% aqueous sodium thiosulfate $Na_2S_2O_3$ (600 mL), water (1 L), and brine solution (600 mL). The organic layer was dried on $Na_2SO_4$ (150 grams). The organic layer ("Reaction Mass 1") as such was used for the next step.

Step 2

A 1.0 molar solution of vinyl magnesium bromide in tetrahydrofuran (4.5 L) was placed in a flask, under a nitrogen atmosphere. Dichloromethane (0.9 L) was added slowly and the mixture was cooled to 25° C. The above Reaction Mass 1 in dichloromethane was added dropwise over a period of 30 minutes, followed by stirring the mixture at a temperature of 25-30° C. for about 2 hours. After completion of the reaction, aqueous saturated ammonium chloride solution (1.5 L) was added at 5-20° C. Dichloromethane (750 mL) was added and the mixture stirred for 15 minutes. The two layers were separated and the organic layer was washed with 10% hydrochloric acid (2.5 L), followed by 5% hydrochloric acid (2×2.5 L), water (2.25 L), saturated sodium bicarbonate ($NaHCO_3$) solution (1.5 L), water (2×2.25 L), and finally brine solution (1.5 L). The organic layer was concentrated at 45° C. to get a thick semi solid (1S,2S)-(2-hydroxy-1-phenyl-but-3-enyl)-carbamic acid t-butyl ester.

Weight: 168 grams
Yield: 100%
Purity: 74%
Chiral purity: 98-99%

EXAMPLE 3

Preparation of (4S,5R)-2,2-dimethyl-4-phenyl-5-vinyl-oxazolidine-3-carboxylic acid tert-butyl ester (IV)

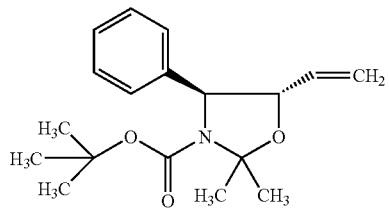

(IV)

(1S,2S)-(2-hydroxy-1-phenyl-but-3-enyl)-carbamic acid tert-butyl ester (160 grams, 0.608 mole) was dissolved in toluene (1600 mL). Dimethoxypropane (745 mL, 6.08 mole) was added at temperature in the range of 20-40° C. followed by addition of pyridinium p-toluene sulphonate (2.3 grams, 0.00912 mole). The mixture was heated to 80-85° C., and stirred at the same temperature for about 2-3 hours. The reaction mixture was cooled to 45° C., neutralized with pyridine (3 mL), and concentrated under reduced pressure to get the semi-solid compound (4S,5R)-2,2-dimethyl-4-phenyl-5-vinyl-oxazolidine-3-carboxylic acid tert-butyl ester.

The compound was dissolved in a minimum quantity of DCM and spread over a layer of silica gel (100-200 mesh). After drying, this impregnated silica gel was placed over a layer of silica gel (100-200 mesh) and filled into a column to a height of 4 feet (1.2 meters). The column was washed initially with petroleum ether and later with increasing concentrations of ethyl acetate in petroleum ether varying from 0-3%. The fractions were checked for the desired compound. The fractions containing the compound were collected and evaporated to get the compound as a light yellow syrup, which was further purified by column chromatography using petroleum ether and ethyl acetate and was purified by distillation at 120° C. to 140° C. at 1 to 5 mm vacuum.

Weight: 85 grams
Yield: 50%
Purity: 70-75%
Chiral purity: 97-99%

EXAMPLE 4

Preparation of (4S,5R)-5-carboxymethyl-2,2-dimethyl-4-phenyl-oxazolidine-3-carboxylic acid t-butyl ester (I)

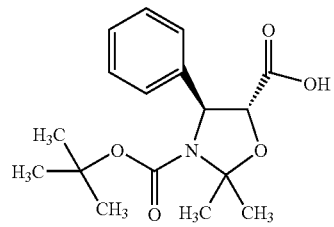

I (4S,5R)-2,2-dimethyl-4-phenyl-5-vinyl-oxazolidine-3-carboxylic acid t-butyl ester (75 grams, 0.25 mole) was dissolved in acetonitrile (450 mL). Carbon tetrachloride (450 mL) and water (750 mL) were added, followed by addition of sodium bicarbonate (135 grams, 1.36 mole) at a temperature in the range of 20-40° C. The reaction mixture was stirred for 15 minutes and sodium metaperiodate (291 grams, 2.18 mole) was added in small portions over a period of 30 minutes. Ruthenium trichloride (8.2 grams, 0.039 mole) was added to reaction mixture at a temperature of 20-40° C. and stirred for about 36 hours. The reaction mass was filtered and the filtrate was washed with ethyl acetate (3×750 mL), then the aqueous layer was cooled to 10-15° C. and acidified with 10% aqueous hydrochloric acid (2 L) to a pH of 2-3. The aqueous layer was extracted with ethyl acetate (3×1 L) and combined organic layer was washed with 2% aqueous $Na_2S_2O_3$ (600 mL) and brine solution (500 mL). The organic layer was concentrated at 50° C. under vacuum to get a thick semi-solid, which was then triturated with petroleum ether (25 mL) and filtered to get the desired white solid (4S,5R)-5-carboxymethyl-2,2-dimethyl-4-phenyl-oxazolidine-3-carboxylic acid tert-butyl ester (I).

Weight: 55.61 grams
Yield: 70%
Purity: 95-97%
Chiral purity: 98-99%

The invention claimed is:

1. A process for preparing the compound of Formula I

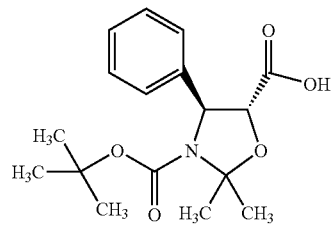

I comprising:
(i) reacting phenylglycinol with a reagent for introducing a t-butoxycarbonyl group, to obtain the compound of Formula II

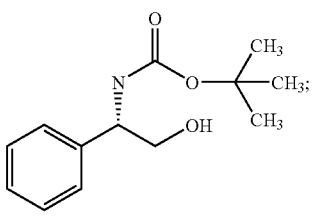

(ii) oxidizing the compound of Formula II and then reacting an obtained carbonyl intermediate with vinyl magnesium halide to obtain the compound of Formula III

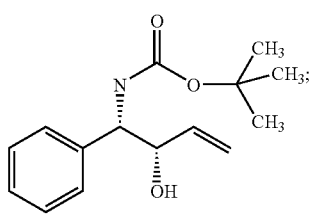

(iii) reacting the compound of Formula III with 2,2-dimethoxypropane to obtain the compound of Formula IV

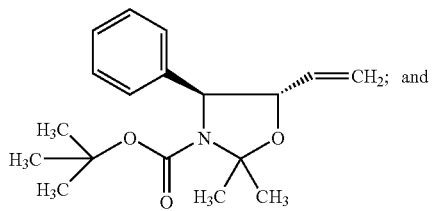

(iv) oxidizing the compound of Formula IV.

2. The process of claim 1, wherein oxidizing in (ii) comprises reacting with an oxidizing agent, in the presence of a catalyst.

3. The process of claim 1, wherein oxidizing in (ii) comprises reacting with an oxidizing agent, in the presence of a catalyst comprising 2,2,6,6-tetramethylpiperidine-N-oxide.

4. The process of claim 1, wherein oxidizing in (ii) comprises reacting with a hypochlorite salt, in the presence of a catalyst comprising 2,2,6,6-tetramethylpiperidine-N-oxide.

5. The process of claim 1, wherein the compound of Formula IV is purified prior to oxidizing in (iv).

6. The process of claim 1, wherein the compound of Formula IV is purified by column chromatography, prior to oxidizing in (iv).

7. The process of claim 1, wherein oxidizing in (iv) comprises reacting with an alkali metal periodate.

8. The process of claim 1, wherein oxidizing in (iv) comprises reacting with an alkali metal periodate, in the presence of a catalyst comprising a ruthenium salt.

9. A process comprising:
(i) reacting phenylglycinol with a reagent for introducing a t-butoxycarbonyl group, to produce (1S)-(2-hydroxy-1-phenyl-ethyl)-carbamic acid t-butyl ester;
(ii) oxidizing the product of (i) and then reacting an obtained carbonyl intermediate with vinyl magnesium halide to produce (1S,2S)-(2-hydroxy-1-phenyl-but-3-enyl)carbamic acid t-butyl ester;
(iii) reacting the product of (ii) with 2,2-dimethoxypropane to produce (4S,5R)-2,2-dimethyl-4-phenyl-5-vinyl-oxazolidine-3-carboxylic acid t-butyl ester; and
(iv) oxidizing the product of (iii) to produce (4S,5R)-5-carboxymethyl-2,2-dimethyl-4-phenyl-oxazolidine-3-carboxylic acid t-butyl ester.

10. The process of claim 9, wherein the reagent in (i) comprises di-t-butyl dicarbonate.

11. The process of claim 9, wherein the oxidizing in (ii) comprises reacting with a hypochlorite compound.

12. The process of claim 11, wherein oxidizing in (ii) occurs in the presence of a catalyst comprising 2,2,6,6-tetramethylpiperidine-N-oxide.

13. The process of claim 9, wherein the oxidizing in (iv) comprises reacting with an alkali metal periodate.

14. The process of claim 13, wherein oxidizing in (iv) occurs in the presence of a catalyst comprising a ruthenium salt.

15. The process of claim 9, wherein (4S,5R)-2,2-dimethyl-4-phenyl-5-vinyl-oxazolidine-3-carboxylic acid t-butyl ester is purified, prior to the oxidizing in (iv).

16. The process of claim 9, wherein (4S,5R)-2,2-dimethyl-4-phenyl-5-vinyl-oxazolidine-3-carboxylic acid t-butyl ester is purified by chromatography, prior to the oxidizing in (iv).

17. A process comprising:
(i) reacting phenylglycinol with di-t-butyl dicarbonate, to produce (1S)-(2-hydroxy-1-phenyl-ethyl)-carbamic acid t-butyl ester;
(ii) reacting the product of (i) with a hypochlorite compound, and then reacting an obtained carbonyl intermediate with vinyl magnesium halide to produce (1S,2S)-(2-hydroxy-1-phenyl-but-3-enyl)carbamic acid t-butyl ester;
(iii) reacting the product of (ii) with 2,2-dimethoxypropane to produce (4S,5R)-2,2-dimethyl-4-phenyl-5-vinyl-oxazolidine-3-carboxylic acid t-butyl ester;
(iv) purifying (4S,5R)-2,2-dimethyl-4-phenyl-5-vinyl-oxazolidine-3-carboxylic acid t-butyl ester; and
(v) reacting purified (4S,5R)-2,2-dimethyl-4-phenyl-5-vinyl-oxazolidine-3-carboxylic acid t-butyl ester with an alkali metal periodate to produce (4S,5R)-5-carboxymethyl-2,2-dimethyl-4-phenyl-oxazolidine-3-carboxylic acid t-butyl ester.

18. The process of claim 17, wherein reacting with a hypochlorite compound in (ii) occurs in the presence of a catalyst comprising 2,2,6,6-tetramethylpiperidine-N-oxide.

19. The process of claim 17, wherein purifying in (iv) comprises chromatography on silica gel.

20. The process of claim 17, wherein reacting with an alkali metal periodate in (v) occurs in the presence of a catalyst comprising a ruthenium salt.

* * * * *